United States Patent

Pugin et al.

Patent Number: 5,244,857
Date of Patent: Sep. 14, 1993

[54] DIPHOSPHINES CONTAINING SILANE GROUPS, IMMOBILISE DIPHOSPHINES AND THE USE THEREOF AS HYDROGENATION CATALYSTS

[75] Inventors: Benoît Pugin, Münchenstein; Manfred Müller, Dagmersellen; Felix Spindler, Starrkirch-Wil, all of Switzerland

[73] Assignee: Ciba-Geigy Corporation, Ardsley, N.Y.

[21] Appl. No.: 823,517

[22] Filed: Jan. 21, 1992

[30] Foreign Application Priority Data

Jan. 25, 1991 [CH] Switzerland .............. 219/91

[51] Int. Cl.$^5$ .............................................. B01J 31/00
[52] U.S. Cl. ........................ 502/167; 502/162; 502/200; 502/208; 502/232; 548/400; 548/406; 548/412; 548/495
[58] Field of Search .......... 502/162, 167, 200, 208, 502/232; 548/400, 406, 412, 495

[56] References Cited

U.S. PATENT DOCUMENTS

| | | | |
|---|---|---|---|
| 4,424,312 | 1/1984 | Stille | 525/274 |
| 4,994,615 | 2/1991 | Spindler et al. | |
| 4,996,361 | 2/1991 | Cullen et al. | |
| 5,011,995 | 4/1991 | Pugin et al. | |

OTHER PUBLICATIONS

Chemische Berichte, 119 No. 11 pp. 3326-3343 (1986).
Ichiwa, J. Chem. Jap. Soc., Chemistry Letters pp. 905-908 (1978).
Nagel, et al. J. Chem. Soc., Chem. Commun., pp. 1098-1099 (1986).

Primary Examiner—Patrick P. Garvin
Assistant Examiner—Brent M. Peebles
Attorney, Agent, or Firm—Kevin T. Mansfield; Edward McC. Roberts

[57] ABSTRACT

Compounds of formula II

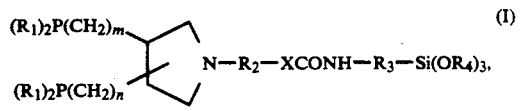

wherein the groups $(R_1)_2P(CH_2)_m$ and $n$ are in o- or m-position to each other and the substituents $R_1$ are identical or different radicals, m and n are each independently of the other 0 or 1, $R_1$ is linear or branched $C_1-C_{12}$alkyl, unsubstituted $C_5-C_6$cycloalkyl or $C_5-C_6$cycloalkyl which is substituted by $C_1-C_4$alkyl or $C_1-C_4$alkoxy, or is phenyl or benzyl, or both substituents $R_1$ in a group $(R_1)_2P$ together are o,o'-diphenylene, —$R_2$—X— is a bond or —$(C_xH_{2x}-O)_y$—, or X— is O— and $R_2$ is $C_1-C_6$alkylene, x is an integer from 2 to 6 and y is an integer from 2 to 6, $R_3$ is $C_2-C_{18}$alkylene, phenylene or benzylene, and $R_4$ is $C_1-C_6$alkyl or phenyl, can be applied to solid carriers, such as silica gel or aerosils, and complexed with rhodium or iridium compounds. These materials are heterogeneous and separable catalysts for the asymmetrical hydrogenation of prochiral compounds containing carbon double bonds or carbon/hetero atom double bonds, for example ketones and imines.

17 Claims, No Drawings

DIPHOSPHINES CONTAINING SILANE GROUPS, IMMOBILISE DIPHOSPHINES AND THE USE THEREOF AS HYDROGENATION CATALYSTS

The present invention relates to pyrrolidine diphosphines which contain silane groups, to said pyrrolidine diphosphines fixed on a solid carrier material and to the use thereof in the form of rhodium or iridium complexes for the hydrogenation of olefinic double bonds and hetero double bonds, especially for enantioselective hydrogenation using chiral pyrrolidine diphosphines.

The enantioselective hydrogenation of ketimines to optically active secondary amines using chiral rhodium and iridium diphosphine complexes as homogeneous catalysts is described in EP-A-0 256 982, EP-A-0 302 021 and EP-A-0 301 457. The expensive catalysts cannot, however, be recovered, or recovery is only possible by complicated separating methods and always with unwanted losses. Moreover, these catalysts lose much of their activity in the course of the first reaction, so that their direct reuse in further hydrogenation processes is allied to high losses of yield and is therefore uneconomic. There is a need for catalysts which can be readily separated and reused while substantially retaining their activity and, in particular, their selectivity.

In J. Chem. Japan. Soc., Chemistry Letters, pages 905 to 908 (1978), K. Achiwa describes polystyrene copolymers whose benzene rings contain pyrrolidine diphosphine-N-carbonyl groups complexed with rhodium. It is difficult to synthesize these monomers, and the hydrogenation of prochiral olefins with these heterogeneous catalysts entails a loss of enantioselectivity.

U. Nagel et al. disclose heterogeneous rhodium catalysts for the enantioselective hydrogenation of α-(acetylamino)cinnamic acid in J. Chem. Soc., Chem. Commun., pages 1098–1099. The catalysts are pyrrolidine diphosphines which are complexed with rhodium and which carry a triethoxysilyl-n-propyldicarboxylic acid monoamide radical at the N-atom. They are applied to silica gel as solid carrier material. The synthesis of these materials is very troublesome. Although comparably good selectivities are obtained as compared with the monomers, the loss of activity is high and diminishes the possibility of reuse.

In one of its aspects the invention relates to compounds of formula I

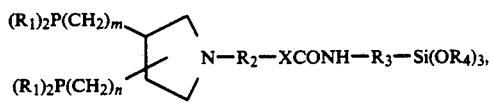
N—R$_2$—XCONH—R$_3$—Si(OR$_4$)$_3$, (I)

wherein the groups $(R_1)_2P(CH_2)_{m\ and\ n}$ are in o- or m-position to each other and the substituents $R_1$ are identical or different radicals, m and n are each independently of the other 0 or 1, $R_1$ is linear or branched $C_1$-$C_{12}$alkyl, unsubstituted $C_5$-$C_6$cycloalkyl or $C_5$-$C_6$-cycloalkyl which is substituted by $C_1$-$C_4$alkyl or $C_1$-$C_4$alkoxy, or is phenyl or benzyl, or both substituents $R_1$ in a group $(R_1)_2P$ together are o,o'-diphenylene, —R$_2$—X— is a bond or —(C$_x$H$_{2x}$—O)$_y$—, or X— is O— and R$_2$ is C$_1$-C$_6$alkylene, x is an integer from 2 to 6 and y is an integer from 2 to 6, R$_3$ is C$_2$-C$_{18}$alkylene, phenylene or benzylene, and R$_4$ is C$_1$-C$_6$alkyl or phenyl.

In the compounds of formula I, the sum of m+n is preferably 0 or 1.

The substituents $R_1$ of a phosphine group are preferably identical radicals and, most preferably, all four substituents $R_1$ are identical radicals.

$R_1$ as alkyl contains preferably 1 to 8, most preferably 1 to 4, carbon atoms. Alkyl is typically methyl, ethyl and the isomers of propyl, butyl, pentyl, hexyl, heptyl, octyl, nonyl, decyl, undecyl and dodecyl. Particularly suitable alkyl and alkoxy substituents are methyl, ethyl, methoxy and ethoxy. Cycloalkyl is typically cyclopentyl and cyclohexyl. In a particularly preferred embodiment of the invention, $R_1$ is phenyl.

In another preferred embodiment of the invention, —R$_2$—X— is a bond.

$R_2$ as alkylene may be linear or branched and contains preferably 2 to 4 and, most preferably, 2 or 3 carbon atoms. Illustrative examples are methylene, ethylene, 1,2- and 1,3-propylene, 1,2-, 1,3-and 1,4-butylen, pentylene and hexylene. Particularly preferred alkylene radicals are ethylene and 1,2-propylene.

In the group —(C$_x$H$_{2x}$—O)$_y$—, x is preferably 2, 3 or 4 and, most preferably, 2 or 3, and y is preferably an integer from 2 to 4. This group will typically be polyoxaethylene containing conveniently 2, 3, 4, 5 or 6 oxaethylene units, or poly-1,2-oxapropylene containing 2, 3, 4, 5 or 6 1,2-oxapropylene units.

$R_3$ as alkylene may be linear or branched and contains preferably 2 to 12 carbon atoms. Illustrative examples are ethylene and the isomers of propylene, butylene, pentylene, hexylene, heptylene, octylene, nonylene, decylene, undecyclene, dodecylene, tridecylene, tetradecylene, hexadecylene and octadecyclene. Preferably $R_3$ is linear or branched alkylene of 3 to 12 carbon atoms, typically 1,3-propylene or 1,11-undecyclene. In another embodiment, $R_3$ is preferably phenylene.

$R_4$ is preferably $C_1$-$C_4$alkyl and, most preferably, methyl or ethyl.

The compounds of formula I are preferably obtained in the form of the optically active isomers, with respect to the position of the phosphine(methyl) groups.

In a particularly preferred embodiment of the invention, $R_1$ is phenyl and —R$_2$X— is a bond, $R_3$ is 1,3-propylene and $R_4$ is methyl or ethyl, and m is 1 and n is 0, and the groups $(R_1)_2P$— and $(R_1)_2PCH_2$— are in m-position, or m and n are each 0 and the groups $(R_1)_2P$— are in o-position.

In another of its aspects, the invention relates to a process for the preparation of compounds of formula I, which comprises reacting a compound of formula II $(R_4O)_3Si$—$R_3$—NCO   (II), wherein $R_3$ and $R_4$ are as previously defined, with a compound of formula III

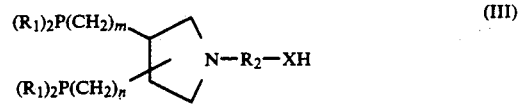
N—R$_2$—XH   (III)

wherein $R_1$, $R_2$, X, m and n are as previously defined.

The compounds of formula II are known and some are commercially available, or they can be prepared by a process described in FR-A-1 371 405. The compounds of formula III, wherein —R$_2$—X— is a bond are also known or can be prepared by known processes. Such processes are described, for example, by U. Nagel in Angew. Chem., 96(6), pages 425–426 (1984) and K.

Achiwa, J. Amer. Chem. Soc., 98(25), pages 8265–8266 (1976).

Compounds of formula III, wherein —$R_2$—X— is the group —$(C_xH_{2x}$—$O)_y$—, are novel and can be obtained in simple manner by reacting the substituted pyrrolidines with oxiranes. Compounds of formula III, wherein X is —O—, and $R_2$ is alkylene, can be obtained by reacting the pyrrolidines with appropriate halogenated alcohols or with one equivalent of oxirane.

The reaction of the isocyanates of formula II with the compounds of formula III can be carried out at room temperature or elevated temperature, as in the range from 0° to 100° C. The concurrent use of a solvent is expedient, for example a hydrocarbon (petroleum ether, pentane, hexane, cyclohexane, methyl cyclohexane, benzene, toluene or xylene), or a halogenated hydrocarbon (methylene chloride, chloroform, 1,1,2,2-tetrachloroethane and chlorobenzene). The reaction of the hydroxyl group containing compounds of formula III is conveniently carried out in the presence of a catalyst, such as a tin compound or a tertiary organic amine. An excess of isocyanate can be removed after the reaction by the reaction with an alkanol. The isolation and purification of the inventive compounds can be effected by conventional methods, as by distillation or chromatographic methods.

The inventive compounds are normally oily liquids which can be used as chiral ligands for iridium (I) and rhodium (I) complex salts which are excellent homogeneous enantioselective hydrogenation catalysts. The preparation of such catalysts is disclosed, inter alia, in EP-A-0 256 982. The inventive compounds are particularly suitable for preparing heterogeneous and enantioselective hydrogenation catalysts by fixing said compounds on a solid carrier material.

The invention further relates to a solid carrier material which contains diphosphine rhodium or iridium complexes fixed on the surface thereof, which carrier material has the formula IV or IVa

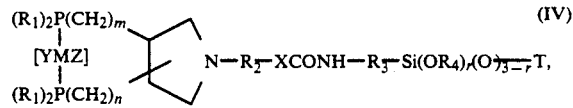

(IV)

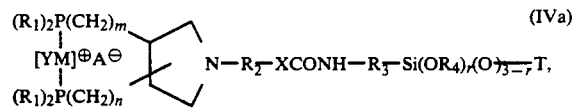

(IVa)

wherein Y denotes two monoolefin ligands or a diene ligand, M is Ir(I) or Rh(I), Z is —Cl, —Br or —I, $A^\ominus$ is the anion of an oxyacid or complex acid, T is a solid carrier material, r is 0, 1 or 2, and $R_1$, $R_2$, $R_3$, $R_4$, X, m and n are as previously defined. $R_1$, $R_2$, $R_3$, $R_4$, X, m and n have the same preferred meanings as given for the compounds of formula I.

A monoolefin ligand Y contains preferably 2 to 6, most preferably 2 to 4, carbon atoms. Illustrative examples are hexene, pentene, butene, propene and, preferably, ethene. A diene ligand Y contains preferably 4 to 8, most preferably 6 to 8, carbon atoms. The dienes may be open-chain or cyclic dienes whose olefin groups are preferably linked through one or two carbon atoms. Preferred dienes are 1,5-hexadiene, 1,5-cycloactadiene and norbornadiene.

Z in formula IV is preferably —Cl or —Br. $A^\ominus$ in formula IVa is preferably $ClO_4^\ominus$, $CF_3SO_3^\ominus$, $BF_4^\ominus$, $B(phenyl)_4^\ominus$, $PF_6^\ominus$, $SbCl_6^\ominus$, $AsF_6^\ominus$ or $SbF_6^\ominus$.

The solid carrier material is preferably selected from silicates and semimetals or metal oxides as well as glasses which are most preferably in the form of powders having average particle diameters of 10 nm to 2000 μm, preferably 10 nm to 1000 μm and, most preferably, 10 nm to 500 μm. The particles may be compact as well as porous particles. Porous particles preferably have high inner surface areas, typically 1 to 1200 $m^2$, preferably 30 to 600 $m^2$. Exemplary of oxides and silicates are $SiO_2$, $TiO_2$, $ZrO_2$, MgO, NiO, $WO_3$, $Al_2O_3$, $La_2O_3$, silica gels, clays and zeoliths. A suitable solid carrier material is also activated carbon. Further, the solid carrier material may also be formed by polysiloxanes which are obtainable by condensing compounds of formula I by themselves or together with alkoxysilanes. Preferred carrier materials are silica gels, aerosils, alumina, titanium oxide and mixtures thereof. Exemplary of a suitable glass carrier material is commercially available controlled pore glass.

The modified carrier material of this invention can be obtained by reacting a solid carrier material which contains diphosphines fixed on the surface thereof and has the formula

(V)

wherein $R_1$, $R_2$, $R_3$, $R_4$, X, T, m, n and r are as previously defined, with a metal compound of formula $[M(Y)Z]_2$ or $M(Y)_2^\oplus A^\ominus$, wherein M, Y, Z and $A^\ominus$ are as previously defined.

The reaction is preferably carried out in an inert gas atmosphere, as under argon, and conveniently in the temperature range from 0° to 40° C., preferably at room temperature. The concurrent use of a solvent or mixture of solvents is advantageous, conveniently selected from the group consisting of hydrocarbons (benzene, toluene, xylene), halogenated hydrocarbons (methylene chloride, chloroform, carbon tetrachloride, chlorobenzene), alkanols (methanol, ethanol, ethylene glycol monomethyl ether), and ethers (diethyl ether, dibutyl ether, ethylene glycol dimethyl ether) or mixtures thereof.

The novel modified material is also obtainable by direct reaction of a hydroxyl group containing solid material, a compound of formula I and a metal compound of formulae $[M(Y)Z]_2$ or $M(Y)_2^\oplus A^\ominus$. The reaction can be carried out stepwise by first adding a solution of the compound of formula I to the solid material, followed by the addition of a solution of the metal compound, or by first dissolving the compound of formula I and the metal compound in a solvent and adding this solution to the solid material. The reaction conditions may be those described previously or hereinafter in connection with the preparation of the material of formula V. The novel modified material can be isolated by filtration and purified by washing with an alkanol and dried under vacuum.

The novel modified material can also be prepared in situ prior to hydrogenation and then used direct as hydrogenation catalyst.

The invention further relates to the solid material of formula V. It can be prepared by reacting compounds of formula I with a hydroxyl group containing carrier material, advantageously in an inert gas atmosphere, as under argon, and in the temperature range from 40° to 180° C. The procedure preferably comprises charging the solid material to a reactor, adding a solution of the compound of formula I, and stirring the mixture at elevated temperature, conveniently in the range from 50° to 110° C. Suitable solvents are those mentioned above. The product is isolated either by decantation or filtration. The residue can be purified by washing with an alkanol and is then dried under a high vacuum.

The novel modified material is preeminently suitable for use as heterogeneous catalyst for the enantioselective hydrogenation of compounds containing prochiral carbon double bonds and carbon/hetero atom double bonds, typically compounds which contain a group selected from C=C, C=N, C=O, C=C—N and C=C—O (q.v. K. E. König, The Applicability of Asymmetric Homogeneous Catalysis, in James D. Morrison (ed.), Asymmetric Synthesis, Vol. 5, Academic Press, 1985). Examples of such compounds are prochiral imines and ketones. The novel catalysts can be separated almsot completely from the reaction mixture after the reaction in simple manner, as by decantation or filtration, and subsequently reused. Compared with other known homogeneous catalysts, there is no or only a minor loss of activity which if desired, can be compensated for by adding minor amounts of fresh catalyst. Furthermore, selectivities (optical yields) are obtained comparable to those of homogeneous catalysts. In the hydrogenation of N-arylketimines with novel iridium catalysts, it has surprisingly been found that, along with comparable selectivities, the novel catalysts even exhibit a higher catalytic activity and a substantially lower deactivation than the homogeneous iridium catalysts disclosed in EP-A-0 256 982 and EP-A-0 301 457.

In another of its aspects, the invention relates to the use of the solid carrier material of formulae IV or IVa as heterogeneous catalyst for the asymmetrical hydrogenation of prochiral compounds containing carbon double bonds or carbon/hetero atom double bonds, especially those containing a C=C, C=N, C=O, C=C—N or C=C—O group. The use for hydrogenating unsymmetrical carbon double bonds, ketimines and ketones is preferred. It is also preferred to use the novel solid carrier material of formulae IV or IVa obtained in the form of the iridium catalyst for hydrogenating prochiral N-arylketimines to optically active secondary amines. The novel solid carrier material of formulae IV or IVa obtained in the form of the rhodium catalyst is preferably used for hydrogenating carbon double bonds, as for example prochiral carbon double bonds.

In yet another of its aspects, the invention relates to a process for the asymmetrical hydrogenation of compounds containing carbon double bonds or carbon/-hetero atom double bonds, which comprises hydrogenating said compounds in the temperature range from −20° to +80° C. and under a hydrogen pressure of $10^5$ to $10^7$ Pa, in the presence of catalytic amounts of a solid carrier material of formula IV or IVa.

Preferred compounds have already been mentioned. Unsymmetrical ketimines and ketones are known. Suitable N-arylketimines are disclosed, for example, in EP-A-0 256 982. N-Aliphatic ketimines are disclosed, for example, in EP-A-0 301 457. Imines can be prepared from the corresponding unsymmetrical ketones, which are known and in some cases commercially available or obtainable by known processes. Suitable unsubstituted or substituted alkenes are described in the publication by K. E. König cited above.

The process is preferably carried out in the temperature range from −20° to +50° C. and preferably under a hydrogen pressure of $1 \cdot 10^5$ to $6 \cdot 10^6$ Pa.

The amount of catalyst will preferably be chosen such that the molar ratio of compound to be hydrogenated to active catalyst component fixed on the solid carrier material is preferably from 2000 to 40, most preferably 800 to 50.

A preferred process comprises additionally using an ammonium or alkali metal chloride, bromide or iodide, especially when using novel iridium catalysts. The amount may be from 0.1 to 100, preferably 1 to 50 and, most preferably, 2 to 20, equivalents, based on the active catalyst component fixed on the solid carrier material. The addition of iodides is preferred. Ammonium is preferably tetraalkylammonium containing 1 to 6 carbon atoms in the alkyl moieties. The preferred alkali metal is lithium, sodium or potassium.

The hydrogenation can be carried out without or in the presence of solvents. Suitable solvents, which may be used alone or in admixture, are typically: aliphatic and aromatic hydrocarbons (pentane, hexane, cyclohexane, methycyclohexane, benzene, toluene, xylene); alcohols (methanol, propanol, butanol, ethylene glycol monomethyl ether); ethers (diethyl ethers, diethylene glycol dimethyl ether, tetrahydrofuran, dioxane); halogenated hydrocarbons (methylene chloride, chloroform, 1,1,2,2-tetrachloroethane, chlorobenzene); carboxylates and lactones (ethyl acetate, butyrolactone, valerolactone); N-substituted acid amides and lactams (dimethyl formamide, N-methylpyrrolidine). Mixtures of an aromatic hydrocarbon and an alcohol, for example toluene/ethanol or benzene/methanol are advantageous.

By means of the inventive hydrogenation process it is possible to obtain optically pure compounds which are useful intermediates for the synthesis of biologically active compounds, especially in the pharmaceutical and agrochemical sectors. Thus, for example, herbicidally active 5-imidazolecarboxylic acid derivatives which can be used for weed control (EP-A-0 207 563) can be obtained from amines, especially N-carbalkoxymethylamines. The optically pure α-aminocarboxylic acid esters are suitable for peptide syntheses.

The following Examples illustrate the invention in more detail. The reactions are carried out under argon. The NMR spectra are recorded with a 250 Mhz spectrophotometer.

PREPARATION OF THE STARTING MATERIALS

EXAMPLE A1:

(2S,4S)-N-[(1'-Triethoxysilylprop-3'-yl)aminocarbonyl]-2-(diphenyl)phosphinmethyl-4-diphenylphosphine-pyrrolidine.

505 mg (1.11 mmol) of (2S,4S)-2-(diphenylphosphine)-4-(diphenylphosphine)methylpyrrolidine (PPM) are dissolved in 10 ml of toluene in a round flask. Then 306 mg (1.2 mmol) of 1-triethoxysilyl-3-isocyanatopropane are added dropwise and the solution is stirred for 60 minutes at 44° C. After cooling, the solvent is removed on a rotary evaporator at 40° C. and the residue is kept for 3 hours under a high vacuum, giving 870 mg of a slightly yellowish viscous oil which still contains some toluene. The crude product can be used direct in the subsequent reactions. Purification is by column chromatography (Merck 60 silica gel, elution with diethyl ether). Mass spectrum: 700 (M+). $^{31}$P-NMR (CDCl$_3$): −8.79 (s), −22.90 (s). $^1$H-NMR (CDCl$_3$): 4.08 (t, 1H, N$\underline{H}$CO).

EXAMPLE A2:

(2S,4S)-N-[(1′-Triethoxysilylundec-11′-yl)aminocarbonyl]-2-(diphenylphosphine)methyl-4-diphenylphosphine-pyrrolidine.

To a solution of 505 mg (1.11 mmol) of PPM in 5 ml of dry methylene chloride are added 420 mg (1.17 mmol) of 1-triethoxysilyl-11-isocyanato-undecane, and the mixture is stirred for 20 hours at room temperature. The solution is charged direct to a column (Merck 60 silica gel) and chromatographed (elution with diethyl ether). The fractions are concentrated at 40° C. under vacuum on a rotary evaporater and dried under a high vaccum, giving 860 mg (95%) of a colourless oil. Mass spectrum: 812 (M+). $^{31}$P-NMR (CDCl$_3$): −8.78(s), −22.92(s).

EXAMPLE A3:

(3R,4R)-N-[(1′-Triethoxysilylprop-3′-yl)aminocarbonyl]-3,4-bis(diphenylphosphine)-pyrrolidine.

A solution of 494 mg (2 mmol) of 1-triethoxysilyl-3-isocyanatopropane in 5 ml of methylene chloride is added dropwise to a solution of 790 mg (1.8 mmol) of (3R,4R)-3,4-bis(diphenylphosphine)-pyrrolidine in 5 ml of dry methylene chloride, and the mixture is stirred for 20 hours at room temperature. The solvent is then removed under vacuum on a rotary evaporator and the residue is dried under a high vacuum. The viscous oil is stirred in 10 ml of hexane and the white precipitate is isolated by filtration, washed with hexane and dried under a high vacuum. Yield: 95%. $^{31}$P-NMR (CDCl$_3$): −11.7 (s). $^1$H-NMR (CDCl$_3$): 3.16 (m, 2H, C$\underline{H}_2$NH).

EXAMPLE A4:

(3R,4R)-N-[(1′-Triethoxysilylundec-11′-yl)aminocarbonyl]-3,4-bis(diphenylphosphine)-pyrrolidine.

870 mg (2.42 mmol) of 1-triethoxysilyl-11-isocyanato-undecane are added dropwise to a solution of 1011 mg (2.3 mmol) of (3R,4R)-bis(diphenylphosphine)pyrrolidine in 5 ml of dry methylene chloride, nd the mixture is stirred for 20 hours at room temperature. The mixtures is then charged direct to a column (Merck 60 silica gel) and chromatographed (elution with diethyl ether). The solvent of the fractions is removed under vacuum at 40° C. on a rotary evaporator and the residue is dried under a high vacuum, giving 1.57 g (79%) of a colourless oil. $^{31}$P-NMR (CDCl$_3$): −11.66 (s). $^1$H-NMR (CDCl$_3$): 3.16 (m, 2H, C$\underline{H}_2$NH).

B) PREPARATION OF CARRIER MATERIALS WITH FIXED LIGANDS

EXAMPLE B1

Compound A1 on silica gel.

With stirring, 2.5 g of silica gel (Merck 100) are dried at 130° C. under a high vacuum and then cooled to room temperature under argon. Then a solution of 260 mg of compound A1 in 15 ml of dry, degassed toluene are added and the mixture is slowly stirred for 5.5 hours at 70° C.. After cooling, the supernatant solution is removed by vacuum filtration from the silica gel, which is washed 5 times with degassed methanol and subsequently dried at 30° C. under a high vacuum. Elemental analysis shows a phosphorus content of 0.69%, corresponding to 111 μmol of fixed compound A1 per g of silica gel.

EXAMPLE B2

Compound A3 on silica gel.

With stirring, 3 g of silica gel (Merck 100) are dried at 130° C. under a high vacuum and then cooled to room temperature under argon. Then a solution of 295 mg of compound A3 in 19 ml of dry toluene is added and the mixture is slowly stirred for 4 hours at 70° C. After cooling, the supernatant solution is removed by vacuum filtration from the silica gel, which is washed with 5×20 ml of degassed methanol and subsequently dried under a high vacuum. Elemental analysis shows a phosphorus content of 0.55%, corresponding to 88.7 μmol of fixed compound A3 per g of silica gel.

EXAMPLE B3

Compound A4 on silica gel.

The procedure of Example B2 is repeated, but using compound A4. Elemental analysis shows a phosphorus content of 0.3%, corresponding to 48. μmol of fixed compound A4 per g of silica gel.

EXAMPLE B4

Compound A1 on silica gel (high ligand loading).

With stirring, 1.5 g of silica gel (Merck 100) are dried at 130° C. under a high vacuum in a 50 ml glass tube reactor and then cooled to room temperature under argon. Then a solution of 407 mg (0.581 mmol) of compound A1 in 7.5 ml of dry, degassed toluene are added and the mixture is slowly stirred for 16 hours at 90° C. After cooling, the supernatant solution is removed by vacuum filtration from the silica gel, which is washed 5 times with degassed methanol and subsequently dried at 30° C. under a high vacuum. Elemental analysis shows a phosphorus content of 1.27%, corresponding to 204 μmol of fixed compound A1 per g of silica gel.

C) PREPARATION OF CATALYSTS

EXAMPLE C1

Rhodium catalyst with compound A1 on aerosil.

In a round flask, 0.7 g of aerosil (MOX 170, Degussa) is repeatedly degassed with argon under a high vacuum and placed under an argon atmosphere. In a second flask, 58.9 mg (0.084 mmol) of compound A1 and 17.3 mg (0.035 mmol) of [Rh(cyclooctadiene)Cl]$_2$ are repeatedly degassed with argon under a high vacuum and then dissolved in 20 ml of dry toluene under argon. The solution is added to the aerosil and the mixture is slowly stirred for 5.5 hours at 60° C.. After cooling, the mixture is centrifuged and the supernatant solution is stripped off. The residue is washed with 5×8 ml of methanol and then dried under a high vacuum at 30° C. Elemental analysis shows a phosphorus content of 0.75% and a rhodium content of 0.95%, corresponding to 121 μmol of fixed compound A1 per g of aerosil and 92 μmol of rhodium complex per g of aerosil.

EXAMPLE C2

Rhodium catalyst with compound A3 on silica gel.

With stirring, 1.3 g of silica gel (Merck 100) are dried at 130° C. for 3 hours under a high vacuum in a round flask, then placed under argon and cooled to room temperature. In a second round flask, 118 mg (0.172 mmol) of compound A3 and 54 mg (0.143 mmol) of Rh(norbornadiend)$_2$BF$_4$ are degassed repeatedly with argon under a high vacuum and dissolved in 8 ml of dry toluene and 1 ml of dry methanol. The solution is added to silica gel and the mixture is slowly stirred for 4.5 hours at 55° C.. After cooling and settling out, the supernatant solution is stripped off and the residue is washed with 5×5 ml of methanol and then dried at 30° C. under a high vacuum. Elemental analysis shows a phosphorus content of 0.75% and a rhodium content of 0.95%, corresponding to 121 μmol of fixed compound A3 per g of aerosil and 92 μmol of rhodium complex per g of silica gel.

EXAMPLE C3

Rhodium catalyst with compound A3 on silica gel.

The procedure of Example C2 is repeated, but using only 8 ml of methanol as solvent. Elemental analysis shows a phosphorus content of 0.33% and a rhodium content of 0.45%, corresponding to 53 μmol of fixed compound A3 per g of aerosil and 44 μmol of rhodium complex per g of aerosil.

D) USE EXAMPLES

EXAMPLE D1

Hydrogenation of methyl (Z)-acetamidocinnamate with rhodium catalyst C2.

44.4 mg (4.1 μmol) of rhodium complex C2 are weighed into a glass reactor and a solution of 4.1 mmol of methyl (Z)-acetamidocinnamate in 13.5 ml of methanol is added under argon. The mixture is introduced under argon pressure into a 50 ml steel autoclave with the aid of a capillary. After flushing with hydrogen and reducing the pressure three times, the hydrogen pressure is set to $5.8 \cdot 10^6$ Pa. The hydrogenation is initiated by activating the stirrer. The conversion is determined by the fall in pressure and analysed by gas chromatography. The conversion is 100% after 85 minutes, and the enantiomer excess (ee) is 85.8%.

The reaction solution is drawn off under argon with a syringe and via a membrane. The catalyst on the membrane is thereafter returned to the autoclave with a fresh reaction solution (4.1 mmol of methyl (Z)-acetamidocinnamate in 13.5 ml of methanol) and hydrogenation is carried out under the same conditions. The conversion is 100% after 210 minutes, ee 84.3%.

EXAMPLE D2

Hydrogenation of methyl (Z)-acetamidocinnamate with rhodium catalyst C3.

The procedure of Example D1 is repeated, using 32 μmol of rhodium catalyst C3 and 3.25 mmol of methyl (Z)-acetamidocinnamate in 11 ml of methanol. The conversion is 100% after 60 minutes, ee 86.6%.

The catalyst is reused as in D1: The conversion is 100% after 90 minutes, ee 86.7%.

EXAMPLE D3

Preparation of the catalyst in situ.

In a round flask, 169 mg (18.8 μmol) of carrier material of Example B1 are dissolved in 5.3 l of tetrahydrofuran. In another round flask, 13.4 μmol of Rh(norbornadiene)$_2$BF$_4$ are dissolved in 2.7 ml of degassed methanol. Both mixtures are combined and stirred until the solution is decolourised. Then a solution of 2.69 mmol of methyl (Z)-acetamidocinnamate in 16 ml of methanol is added to this mixture. The mixture is evacuated and flushed three times with hydrogen, and the hydrogen pressure is set to $10^5$ Pa. The batch is then stirred vigorously. The conversion is 99.9% after 32 minutes, ee 93.5%.

Reuse of the catalyst: The reaction solution is stripped off from the catalyst and then a solution of 2.69 mmol of methyl (Z)-acetamidocinnamate is added. The hydrogen pressure is set to $10^5$ Pa and the batch is stirred vigorously. The conversion is 100% after 16 minutes, ee 94.8%.

EXAMPLE D4

In situ preparation of a catalyst.

150 mg (17 μmol) of the carrier material of Example B1 are charged under argon to a round falsk and, in a second round flask, 6.8 μmol of [Rh(cyclooctadiene)Cl]$_2$ are dissolved under argon in 2.5 ml of toluene and the solution is then added dropwise to the first flask. Afterwards, the mixture is stirred until the solution is decolourised and then a solution of 2.72 mmol of methyl (Z)-acetamidocinnamate in 22 ml of ethanol is added dropwise. The mixture is evacuated and then flushed three times with hydrogen, and the hydrogen pressure is set to $10^5$ Pa. The batch is then stirred vigorously. The conversion is 99.6% after 75 minutes, ee 85%.

Reuse of the catalyst: The reaction solution is stripped off from the catalyst and then a solution of 2.72 mmol of methyl (Z)-acetamidocinnamate is added. Hydrogenation is carried out as previously under a hydrogen pressure of $10^5$ Pa. The conversion is 99% after 32 minutes, ee 82.5%.

EXAMPLE D5

In situ preparation of the catalyst 53.1 mg (4.7 μmol) of the carrier material of Example B2 are weighed into a round flask under argon and, in a second round flask, 3.9 μmol of [Rh(norbornadiene)$_2$]BF$_4$ are dissolved under argon in 1.5 ml of methanol and the solution is added dropwise to the first flask. The batch is then stirred to decolourise the solution. A solution of 4 mmol of methyl (Z)-acetamidocinnamate in 12 ml of methanol is added to this solution and the mixture is introduced under pressure into a 50 ml steel autoclave. The pressure is released and the mixture is flushed three times with hydrogen under a pressure of $5 \cdot 10^6$ Pa, and finally the hydrogen pressure is set to $5.8 \cdot 10^6$ Pa. The batch is subsequently vigorously stirred. The conversion is 100% after 40 minutes, ee 88%. Reuse of the catalyst: The reaction solution is drawn off via a membrane and the catalyst is returned to the autoclave with a solution of of 4 mmol of methyl (Z)-acetamidocinnamate in 12 ml of methanol. Hydrogenation is carried out as described above. The conversion is 100% after 78 minutzes, ee 87.3%.

EXAMPLE D6

Preparation of the catalyst in situ.

The procedure of Example D4 is repeated, but using 2.9 μmol of the carrier material of Example B3, 2.4 μmol of [Rh(norbornadiene)$_2$]BF$_4$ in 0.9 ml of methanol and 4.8 mmol of methyl (Z)-acetamidocinnamate in 14.3 ml of methanol. The conmversion after 95 minutes is 100%, ee 85.5%.

Reuse of the catalyst: The procedure of Example D4 is repeated, but using 5.17 mmol of methyl (Z)-acetamidocinnamate in 15.5 ml of methanol. The conversion after 230 minutes is 100%, ee 88%.

In Examples D1 to D6 the conversion is determined by the drop in pressure and by gas chromatography column SE 54, 15 m). The enantiomer excess (ee) is determined by gas chromatography (column Chirasil-1-Val, 50 m).

EXAMPLE D7

Hydrogenation with iridium catalyst.

10.5 μmol of [Ir(cyclooctadiene)Cl]$_2$, 26.3 μmol of the carrier material of Example B1 and 42 μmol of tetra-n-butylammonium iodide are charged to a round flask together with 6.2 ml of methanol and 6.2 ml of benzene under argon, and the mixture is stirred until the solution is decolourised. Then a solution of 2.01 g (10.5 mmol) of N-(2,6-dimethylphen-1-yl)methoxymethylmethylketimine is added dropwise and the mixture is introduced under pressure into a 50 ml steel autoclave. The mixture is evacuated and flushed with hydrogen three times, and the hydrogen pressure is finally set to 4·10$^6$ Pa. The batch is stirred at 30° C. and the course of the hydrogenation is followed by observing the drop in pressure. The conversion is analysed by gas chromatography. The catalyst is isolated by filtration and the solvent is stripped from the reaction mixture under pressure on a rotary evaporator. The crude product is purified by flash chromatography (silica gel, hexane/ethyl acetate 1:1), and the enantiomer excess is determined by polarimetry (rotation of the (S)-enantiomer [α]$_{365}$ at 20° C.-130.5°, c=3 in hexane). The conversion after 19 hours is 96.5%, ee 62.7%.

Reuse of the catalyst: The supernatant solution is stripped from the catalyst, the same amount of ketimine as before is added and the same procedure is carried out. The conversion after 35 hours is 100%, ee 61.1%.

EXAMPLE D8

Hydrogenation with iridium catalyst.

The procedure of Example D7 is repeated, but using the carrier material of Example B2 and setting the hydrogenation pressure to 9·10$^6$ Pa. The conversion after 6 hours is 100%, ee 29.1%.

EXAMPLE D9

Hydrogenation with rhodium catalyst prepared in situ.

78.6 mg (0.016 μmol) of the carrier material of Example B4 are weighed into a round flask under argon and, in a second round flask, 0.0125 mmol of [Rh(cyclooctadiene)$_2$]BF$_4$ are dissolved under argon in 1 ml of MeOH and the solution is added dropwise to the first flask. The batch is then stirred to decolourise the solution. To this mixture is added a solution of 2.5 mmol of methyl (Z)-acetamidocinnamate in 17.5 ml of methanol and 4 ml of tetrahydrofuran. The mixture is evacuated and flushed three times with hydrogen, and the hydrogen pressure is set to 10$^5$ Pa. The batch is then vigorously stirred. The conversion is 100% after 28 minutes, ee 91.9%. Reuse of the catalyst: The reaction solution is stripped off from the catalyst. Then a solution of 2.5 mmol of methyl (Z)-acetamidocinnamate in 17.5 ml of methanol and 4 ml of tetrahydrofuran is added. The mixture is evacuated once more three times and flushed with hydrogen, and the hydrogen pressure is set to 10$^5$ Pa. The batch is then vigorously stirred. The conversion is 100% after 15 minutes, ee 93.1%.

What is claimed is:

1. A compound of formula I

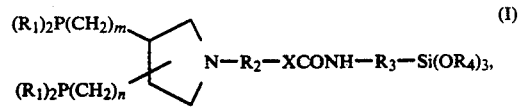

wherein the groups (R$_1$)$_2$P(CH$_2$)$_m$ and n are in o- or m-position to each other and the substituents R$_1$ are identical or different radicals, m and n are each independently of the other 0 or 1, R$_1$ is linear or branched C$_1$-C$_{12}$alkyl, unsubstituted C$_5$-C$_6$cycloalkyl or C$_5$-C$_6$-cycloalkyl which is substituted by C$_1$-C$_4$alkyl or C$_1$-C$_4$alkoxy, or is phenyl or benzyl, or both substituents R$_1$ in a group (R$_1$)$_2$P together are o,o'-diphenylene, —R$_2$—X— is a bond or —(C$_x$H$_{2x}$—O)$_y$—, or X— is O— and R$_2$ is C$_1$-C$_6$alkylene, x is an integer from 2 to 6 and y is an integer from 2 to 6, R$_3$ is C$_2$-C$_{18}$alkylene, phenylene or benzylene, and R$_4$ is C$_1$-C$_6$alkyl or phenyl.

2. A compound of formula I according to claim 1, wherein the sum of m+n is 0 or 1.

3. A compound of formula I according to claim 1, wherein R$_1$ is phenyl.

4. A compound of formula I according to claim 1, wherein —R$_2$—X— is a bond.

5. A compound of formula I according to claim 1, wherein R$_3$ is linear or branched C$_2$-C$_{12}$-alkylene.

6. A compound of formula I according to claim 1, wherein R$_4$ is methyl or ethyl.

7. A compound according to claim 1 which is in the form of the optically active isomers, with respect to the position of the phosphine(methyl) groups.

8. A compound of formula I according to claim 1, wherein R$_1$ is phenyl and —R$_2$X— is a bond, R$_3$ is 1,3-propylene and R$_4$ is methyl or ethyl, and m is 1 and n is 0, and the groups (R$_1$)$_2$P- and (R$_1$)$_2$PCH$_2$- are in m-position, or m and n are each 0 and the groups (R$_1$)$_2$P- are in o-position.

9. A solid carrier material which contains a diphosphine rhodium or iridium complex fixed on the surface thereof, which carrier material has the formula IV or IVa

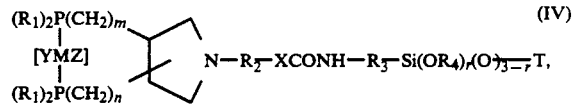

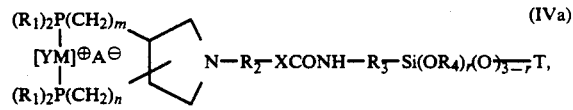

wherein Y denotes two monoolefin ligands or a diene ligand, M is Ir(I) or Rh(I), Z is —Cl, —Br or —I, A$^\ominus$ is the anion of an oxyacid or complex acid, T is a solid carrier material, r is 0, 1 or 2, m and n are m and n are each independently of the other 0 or 1, R$_1$ is linear or branched C$_1$-C$_{12}$alkyl, unsubstituted C$_5$-C$_6$cycloalkyl or C$_5$-C$_6$cycloalkyl which is substituted by C$_1$-C$_4$alkyl or C$_1$-C$_4$alkoxy, or is phenyl or benzyl, or both substituents R$_1$ in a group (R$_1$)$_2$P together are o,o'-diphenylene, —R$_2$—X— is a bond or —(C$_x$H$_{2x}$—O)$_y$—, or X— is O— and $R_2$ is $C_1$-$C_6$alkylene, x is an integer from 2 to 6 and y is an integer from 2 to 6, $R_3$ is $C_2$-$C_{18}$alkylene, phenylene or benzylene, and $R_4$ is $C_1$-$C_6$alkyl or phenyl.

10. A carrier material according to claim 9, wherein Y in formulae IV and IVa is 1,5-hexadiene, 1,5-cyclooctadiene or norbornadiene.

11. A carrier material according to claim 9, wherein Z in formula IV is —Cl or —Br.

12. A carrier material according to claim 9, wherein $A^\ominus$ in formula IVa is $ClO_4^\ominus$, $CF_3SO_3^\ominus$, $BF_4^\ominus$, $B(phenyl)_4^\ominus$, $PF_6^\ominus$, $SbCl_6^\ominus$, $AsF_6^\ominus$ or $SbF_6^\ominus$.

13. A carrier material according to claim 9 which is a silicate, a semimetal or a metal oxide.

14. A carrier material according to claim 13 which is a powder.

15. A carrier material according to claim 13, which is a silica gel, an aerosil, an alumina, a titanium oxide or a mixture thereof.

16. A process for the preparation of a solid carrier material of formula IV or IVa according to claim 10, which comprises reacting a solid carrier material which contains diphosphines fixed on the surface thereof and has the formula

wherein $R_1$, $R_2$, $R_3$, $R_4$, X, T, m, n and r are as defined in claim 9, with a metal compound of formula $[M(Y)Z]_2$ or $M(Y)_2^\oplus A^\ominus$, wherein M, Y, Z and $A^\ominus$ are as defined in claim 10.

17. A solid modified carrier material of formula V

wherein $R_1$, $R_2$, $R_3$, $R_4$, X, T, m, n and r are as defined in claim 9.

* * * * *